United States Patent
Hu

(10) Patent No.: US 9,928,717 B2
(45) Date of Patent: Mar. 27, 2018

(54) HUMAN BODY TUMBLING DETECTION METHOD AND DEVICE AND MOBILE TERMINAL SYSTEM

(71) Applicant: Shenzhen ZhiYing Technologies Co., Ltd., Shenzhen, Guangdong OT (CN)

(72) Inventor: Kun Hu, Guangdong (CN)

(73) Assignee: Shenzhen ZhiYing Technologies Co., Ltd., Shenzhen (CN)

( * ) Notice: Subject to any disclaimer, the term of this patent is extended or adjusted under 35 U.S.C. 154(b) by 28 days.

(21) Appl. No.: 15/084,508

(22) Filed: Mar. 30, 2016

(65) Prior Publication Data

US 2016/0210835 A1    Jul. 21, 2016

Related U.S. Application Data

(63) Continuation of application No. PCT/CN2014/087996, filed on Sep. 30, 2014.

(30) Foreign Application Priority Data

Sep. 30, 2013    (CN) .......................... 2013 1 0469682

(51) Int. Cl.
  *G08B 23/00* (2006.01)
  *G08B 21/04* (2006.01)
  *A61B 5/11* (2006.01)

(52) U.S. Cl.
  CPC .......... *G08B 21/043* (2013.01); *A61B 5/1117* (2013.01)

(58) Field of Classification Search
  CPC .......................... G08B 21/043; A61B 5/1117
  USPC ........................................................ 340/573.1
  See application file for complete search history.

(56) References Cited

U.S. PATENT DOCUMENTS

| 5,982,573 | A  | * | 11/1999 | Henze    | G11B 5/54    |
|           |    |   |         |          | 360/60       |
| 7,369,345 | B1 | * | 5/2008  | Li       | G11B 5/5582  |
|           |    |   |         |          | 360/73.03    |
| 8,676,532 | B2 | * | 3/2014  | Shibata  | G01P 15/0891 |
|           |    |   |         |          | 702/141      |
| 8,990,041 | B2 | * | 3/2015  | Grabiner | A61B 5/1116  |
|           |    |   |         |          | 280/730.1    |
| 9,005,141 | B1 | * | 4/2015  | Najafi   | A61B 5/1116  |
|           |    |   |         |          | 600/587      |
| 9,020,476 | B2 | * | 4/2015  | Leipzig  | H04W 8/22    |
|           |    |   |         |          | 455/416      |
| 9,138,174 | B2 | * | 9/2015  | Jin      | A61B 5/0002  |

(Continued)

*Primary Examiner* — Zhen Y Wu

(57) ABSTRACT

A human body tumbling detection method and device and a mobile terminal system are disclosed. The method may include: when detecting that resultant acceleration of a human body is less than a low acceleration threshold $a_0$, capturing a resultant acceleration sequence $I_0$ within fixed time; in a two-dimensional coordinate system using resultant acceleration and time as coordinate axes and $a_0$ as a reference line, calculating a curve area above the reference line and a curve area below the reference line that are enclosed by curves in $I_0$ coordinates and the reference line; and when a difference between the curve area above the reference line and the curve area below the reference line is less than a curve area threshold $\Delta S$, and time occupied by resultant acceleration below the reference line is greater than a low acceleration time threshold $\Delta T$, determining that the human body tumbles.

12 Claims, 11 Drawing Sheets

(56) References Cited

U.S. PATENT DOCUMENTS

| | | | | |
|---|---|---|---|---|
| 9,402,568 | B2* | 8/2016 | Barfield | G01P 15/0891 |
| 9,589,442 | B2* | 3/2017 | Barfield, Jr. | G08B 21/0446 |
| 9,818,281 | B2* | 11/2017 | Narasimhan | G08B 21/043 |
| 9,835,644 | B2* | 12/2017 | Ten Kate | G01P 7/00 |
| 2005/0099719 | A1* | 5/2005 | Katai | G01P 15/00 |
| | | | | 360/75 |
| 2006/0070439 | A1* | 4/2006 | Kwon | G01P 15/00 |
| | | | | 73/488 |
| 2009/0031803 | A1* | 2/2009 | Noda | G01P 15/0891 |
| | | | | 73/488 |
| 2011/0149431 | A1* | 6/2011 | Shibata | G01P 15/18 |
| | | | | 360/75 |
| 2012/0232823 | A1* | 9/2012 | Baggen | A61B 5/1117 |
| | | | | 702/104 |
| 2014/0062702 | A1* | 3/2014 | Rubio Andres | G08B 21/043 |
| | | | | 340/573.1 |
| 2014/0197945 | A1* | 7/2014 | Gu | G08B 21/0446 |
| | | | | 340/539.11 |
| 2015/0173654 | A1* | 6/2015 | Belanger | A61B 5/1117 |
| | | | | 600/301 |

\* cited by examiner

HUMAN BODY TUMBLING DETECTION METHOD AND DEVICE AND MOBILE TERMINAL SYSTEM

CROSS-REFERENCE TO RELATED APPLICATIONS

The present application is a Continuation Application of PCT application No. PCT/CN2014/087996 filed on Sep. 30, 2014, which claims the benefit of Chinese Patent Application No. 201310469682.6 filed on Sep. 30, 2013, the contents of which are hereby incorporated by reference.

TECHNICAL FIELD

The present invention relates to human body tumbling detection technologies, and in particular, to a human body tumbling detection method and device and a mobile terminal system.

BACKGROUND

According to statistics from the Centers for Disease Control and Prevention, one third of people who are over 65 years old in the world may tumble every year, and one half of them may tumble again. Nearly 10% of people in a tumbling event may be severely injured and afflicted by diseases, resulting in a heavy medical burden and a great health impairment. The quantity of old people in China will exceed 0.2 billion in 2014, and will reach 0.3 billion in 2025. In 2042, the percentage of old people will exceed 30%. Currently, tumbling of old people has become a major medical and social problem. How to reduce impairments caused by tumbling of old people has become a new hot topic of research at home and aboard. The purpose is to reduce the medical burden of a medical security system and the medical burden of children of old people. In particular, the research is of great practical value for old people who live alone away from their children or who often go out.

Currently, some tumbling detection devices are already available in China, but most of them are based on a particular device. Old people need to wear the devices additionally, and it is quite inconvenient. In some related detection methods, a wrong determining rate is high due to limitations of information processing methods and devices or because motion behaviors of a human body are not fully considered.

SUMMARY

A main objective of the present invention is to provide a human body tumbling detection method that can improve accuracy in determining tumbling.

The present invention provides a human body tumbling detection method, including:

when detecting that resultant acceleration of a human body is less than a low acceleration threshold $a_0$, capturing a resultant acceleration sequence $I_0$ within fixed time;

in a two-dimensional coordinate system using resultant acceleration and time as coordinate axes and $a_0$ as a reference line, calculating a curve area above the reference line and a curve area below the reference line that are enclosed by curves in $I_0$ coordinates and the reference line; and when a difference between the curve area above the reference line and the curve area below the reference line is less than a curve area threshold $\Delta S$, and the time occupied by the resultant acceleration below the reference line is greater than a low acceleration time threshold $\Delta T$, determining that the human body tumbles. Preferably, before the step of capturing a resultant acceleration sequence $I_0$ within fixed time when detecting that resultant acceleration of a human body is less than a low acceleration threshold $a_0$, the method further includes:

capturing speed information in a human body tumbling process in one or more human body tumbling samples, where the speed information includes resultant acceleration, speed, and time; and analyzing characteristics of the speed information, calculating and extracting the low acceleration threshold $a_0$, the resultant acceleration sequence $I_0$ within the fixed time, a high acceleration threshold $a_1$, the curve area threshold $\Delta S$, and the low acceleration time threshold $\Delta T$, and establishing a tumbling detection mechanism.

Preferably, the analyzing characteristics of the speed information, calculating and extracting the low acceleration threshold $a_0$, the resultant acceleration sequence $I_0$ within the fixed time, a high acceleration threshold $a_1$, the curve area threshold $\Delta S$, and the low acceleration time threshold $\Delta T$ further includes:

associating the calculated and extracted low acceleration threshold $a_0$, resultant acceleration sequence $I_0$ within the fixed time, high acceleration threshold $a_1$, curve area threshold $\Delta S$, and low acceleration time threshold $\Delta T$ with human body status information corresponding to the sample, where the human body status information includes stature, weight, and/or motion status.

Preferably, after the step of capturing a resultant acceleration sequence $I_0$ within fixed time when detecting that resultant acceleration of a human body is less than a low acceleration threshold $a_0$, the method further includes:

when capturing the resultant acceleration sequence $I_0$, determining whether resultant acceleration greater than a high acceleration threshold $a_1$ is captured in the sequence $I_0$, and if yes, performing the next step.

Preferably, before the step of capturing a resultant acceleration sequence $I_0$ within fixed time when detecting that resultant acceleration of a human body is less than a low acceleration threshold $a_0$, the method further includes:

receiving settings of human body status information, and adjusting $a_0$, $\Delta S$, and/or $\Delta T$ according to the set human body status information.

Preferably, the method further includes:

after determining that tumbling occurs, capturing a current speed sequence of the human body; when current speed is lower than a speed threshold for more than set time, generating alarm prompt information; and when the alarm prompt information is acknowledged or unacknowledged for more than certain time, generating an alarm.

The present invention further provides a human body tumbling detection device, including:

a determining and capturing module, configured to capture a resultant acceleration sequence $I_0$ within fixed time when detecting that resultant acceleration of a human body is less than a low acceleration threshold $a_0$;

an area calculating module, configured to calculate, in a two-dimensional coordinate system using resultant acceleration and time as coordinate axes and $a_0$ as a reference line, a curve area above the reference line and a curve area below the reference line that are enclosed by curves in $I_0$ coordinates and the reference line; and a tumbling determining module, configured to determine, when a difference between the curve area above the reference line and the curve area below the reference line is less than a curve area threshold $\Delta S$, and time occupied by resultant acceleration below the reference line is greater than a low acceleration time threshold $\Delta T$, that the human body tumbles.

Preferably, the device further includes:

a sample capturing module, configured to capture speed information in a human body tumbling process in one or more human body tumbling samples, where the speed information includes resultant acceleration, speed, and time; and an analyzing and extracting module, configured to analyze characteristics of the speed information, calculate and extract the low acceleration threshold $a_0$, the resultant acceleration sequence $I_0$ within the fixed time, a high acceleration threshold $a_1$, the curve area threshold $\Delta S$, and the low acceleration time threshold $\Delta T$, and establish a tumbling detection mechanism.

Preferably, the analyzing and extracting module is further configured to:

associate the calculated and extracted low acceleration threshold $a_0$, resultant acceleration sequence $I_0$ within the fixed time, high acceleration threshold $a_1$, curve area threshold $\Delta S$, and low acceleration time threshold $\Delta T$ with human body status information corresponding to the sample, where the human body status information includes stature, weight, and/or motion status.

Preferably, the device further includes:

a high acceleration determining module, configured to: when the resultant acceleration sequence $I_0$ is captured, determine whether resultant acceleration greater than a high acceleration threshold $a_1$ is captured in the sequence $I_0$, and if yes, calculate the curve areas by using the area calculating module.

Preferably, the device further includes:

a setting receiving module, configured to receive settings of human body status information, and adjust $a_0$, $\Delta S$, and/or $\Delta T$ according to the set human body status information.

Preferably, the device further includes:

an alarm prompt module, configured to: after it is determined that tumbling occurs, capture a current speed sequence of the human body; when current speed is lower than a speed threshold for more than set time, generate alarm prompt information; and when the alarm prompt information is acknowledged or unacknowledged for more than certain time, generate an alarm.

The present invention further provides a mobile terminal system, including:

an information acquiring module, configured to acquire speed information by using a tri-axis accelerometer;

a determining and capturing module, configured to capture a resultant acceleration sequence $I_0$ within fixed time when detecting that resultant acceleration of a human body is less than a low acceleration threshold $a_0$;

an area calculating module, configured to calculate, in a two-dimensional coordinate system using resultant acceleration and time as coordinate axes and $a_0$ as a reference line, a curve area above the reference line and a curve area below the reference line that are enclosed by curves in $I_0$ coordinates and the reference line;

a tumbling determining module, configured to determine, when a difference between the curve area above the reference line and the curve area below the reference line is less than a curve area threshold $\Delta S$, and time occupied by resultant acceleration below the reference line is greater than a low acceleration time threshold $\Delta T$, that the human body tumbles; and an alarm prompt module, configured to: after it is determined that tumbling occurs, capture a current speed sequence of the human body; when current speed is lower than a speed threshold for more than set time, generate alarm prompt information; and when the alarm prompt information is acknowledged or unacknowledged for more than certain time, generate an alarm by using a mobile communication component.

Preferably, the mobile terminal system further includes:

a high acceleration determining module, configured to: when the resultant acceleration sequence $I_0$ is captured, determine whether resultant acceleration greater than a high acceleration threshold $a_1$ is captured in the sequence $I_0$, and if yes, calculate the curve areas by using the area calculating module.

The present invention may be based on a device that has acceleration detection and communication functions such as a smartphone. So long as a user carries a smartphone installed with an application for human body tumbling detection, the application automatically captures and analyzes human body dynamics information based on different features of kinematics and dynamics in safe moving and tumbling of a human body, determines whether the human body tumbles, and generates an alarm notification such as a short message or a call by using advantages of mobile phone communication. In comparison with other tumbling detection devices that need to be purchased or provided additionally, the device according to the present invention has relatively high applicability, featuring a wide range of use, a low price, and portability. Most importantly, motion behavior characteristics of the human body are fully considered, and therefore, a detection rate is increased, and a wrong determining rate is reduced.

The objectives, functional characteristics, and advantages of the present invention are hereinafter further described with reference to embodiments and accompanying drawings.

DESCRIPTION OF EMBODIMENTS

It should be understood that the specific embodiments described herein are merely used to explain the present invention but are not intended to limit the present invention.

Figure 1:
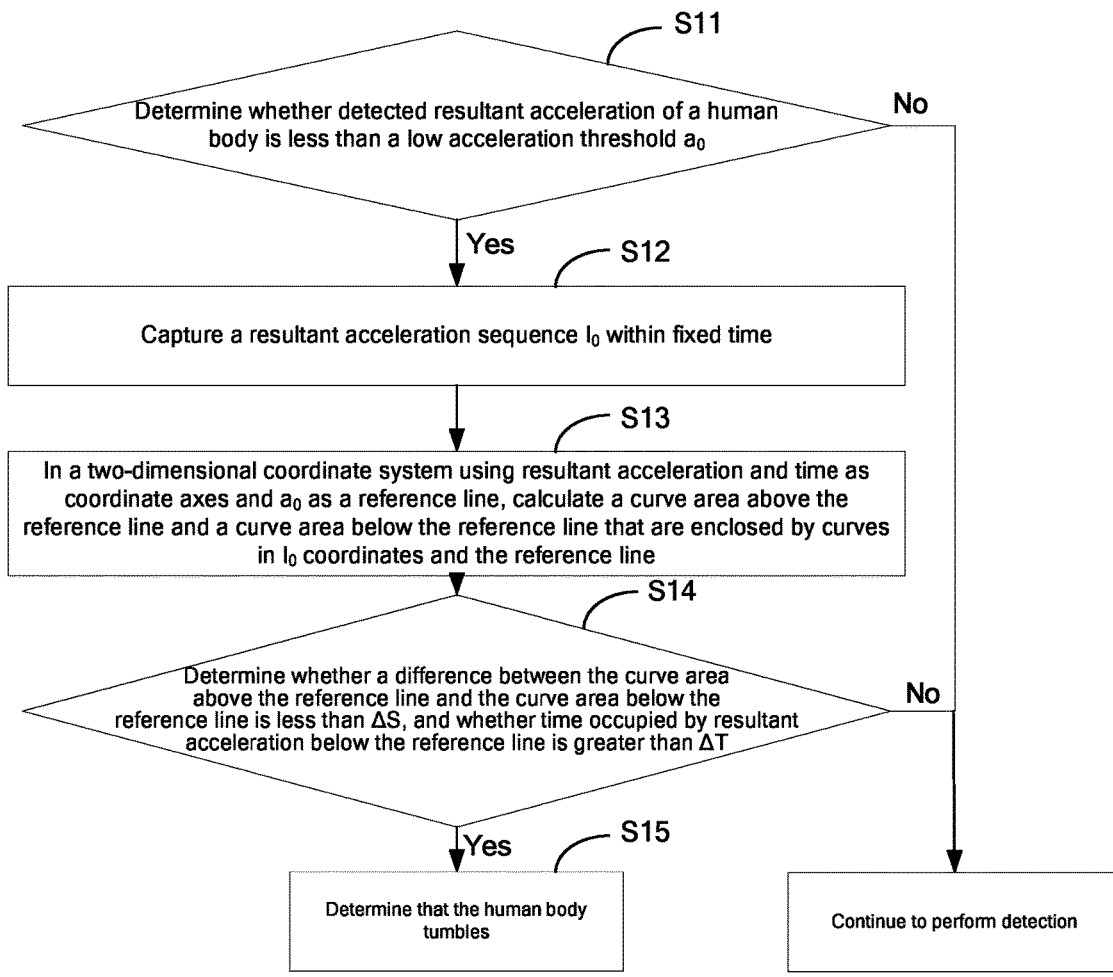
FIG. 1 is a schematic flowchart of steps of an embodiment of a human body tumbling detection method according to the present invention.

Referring to FIG. 1, an embodiment of a human body tumbling detection method according to the present invention is provided. The human body tumbling detection method may include:

Step S11: Determine whether resultant acceleration of a human body is less than a low acceleration threshold $a_0$; if yes, perform step S12; otherwise, continue to perform detection.

Step S12: Capture a resultant acceleration sequence $I_0$ within fixed time.

Step S13: In a two-dimensional coordinate system using resultant acceleration and time as coordinate axes and $a_0$ as a reference line, calculate a curve area above the reference line and a curve area below the reference line that are enclosed by curves in $I_0$ coordinates and the reference line.

Step S14: Determine whether a difference between the curve area above the reference line and the curve area below the reference line is less than a curve area threshold $\Delta S$, and whether time occupied by resultant acceleration below the reference line is greater than a low acceleration time threshold $\Delta T$; if yes, perform step S15; otherwise, continue to perform detection.

Step S15: Determine that the human body tumbles.

In view of the problems that exist in the conventional tumbling detection technologies and detection devices, the human body tumbling detection method provided by the present invention can automatically detect acceleration information and speed information of a human body by using a sensor, correctly determine, according to the acceleration, speed, motion time, and motion status of the human body, whether the human body has tumbled, and prompts whether to generate an alarm for help, and can perform operations such as acknowledging the prompt or canceling the alarm for help.

A device for implementing the human body tumbling detection method needs to be equipped with at least an accelerometer (for example, a tri-axis accelerometer), and when an emergency help function needs to be implemented, may be further equipped with a communication module (for example, a GSM module or a CDMA module for mobile communication). For portability and ease of use, the device may be a mobile terminal, for example, a common mobile terminal device such as a smartphone or a tablet computer. Such common mobile terminal devices are generally equipped with a communication module and an accelerometer, and therefore may be used directly, and no additional configuration is required.

Figure 2:
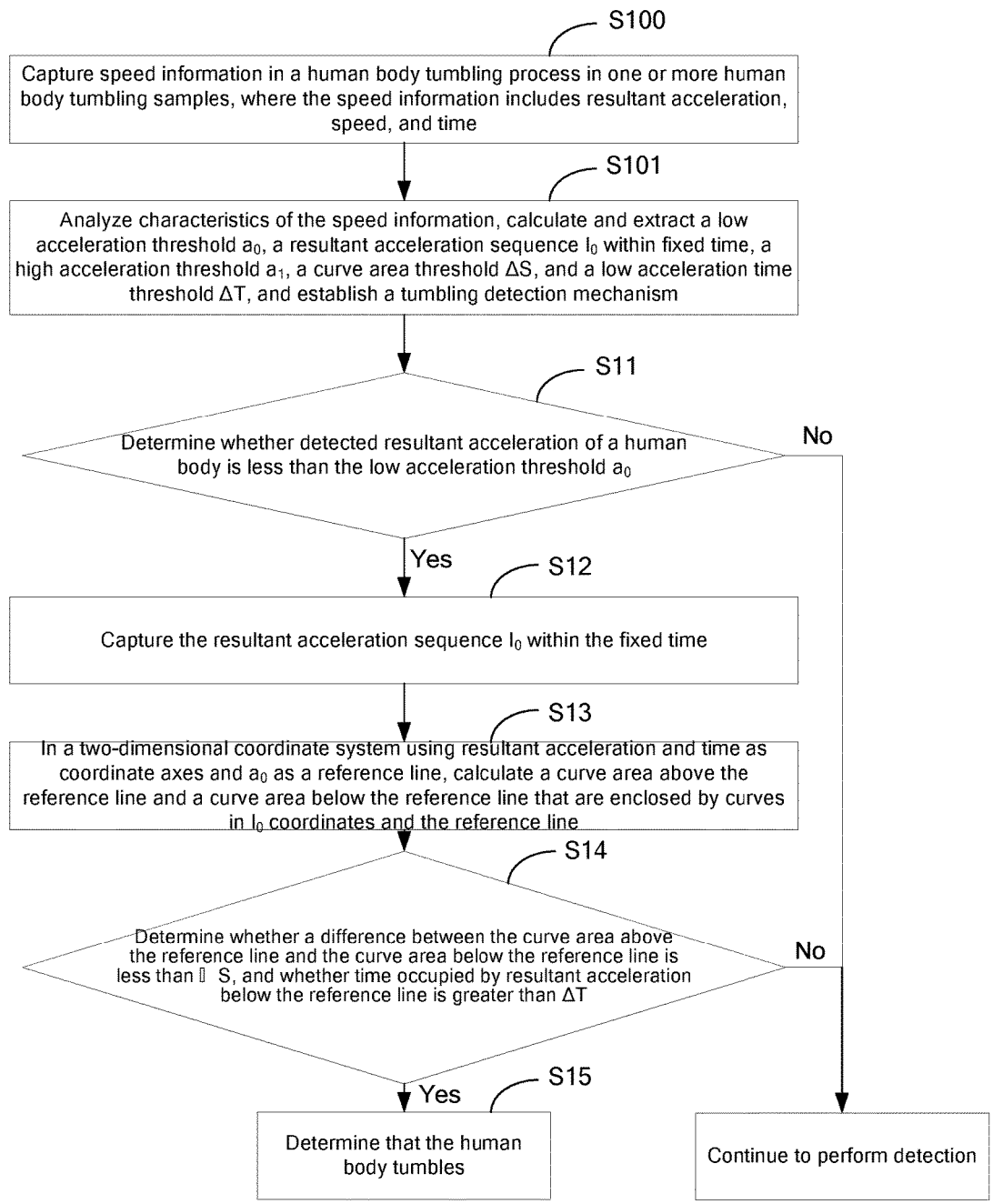
FIG. 2 is another schematic flowchart of steps of an embodiment of a human body tumbling detection method according to the present invention.

Referring to FIG. 2, before step S11, the method may further include:

Step S100: Capture speed information in a human body tumbling process in one or more human body tumbling samples, where the speed information includes resultant acceleration, speed, and time.

Step S101: Analyze characteristics of the speed information, calculate and extract the low acceleration threshold $a_0$, the resultant acceleration sequence $I_0$ within the fixed time, a high acceleration threshold $a_1$, the curve area threshold $\Delta S$, and the low acceleration time threshold $\Delta T$, and establish a tumbling detection mechanism.

Before tumbling detection is implemented, first, several tumbling experiments are performed to capture speed information in a human body tumbling process, where the speed information includes resultant acceleration, speed, and time. Further, an acceleration time sequence before tumbling and bumping may be recorded, some acceleration features are extracted, and a tumbling detection model is established. The model may be trained and optimized continuously by using tumbling data.

Establishment of a tumbling detection model is a most important part for implementing accurate tumbling detection. First, acceleration data related to a tumbling process is acquired according to some experiments and related tumbling data. The acceleration data is analyzed, filtered, and integrated, and features of kinematics and dynamics in human body tumbling, for example, long-time low acceleration before tumbling and possible staggering before tumbling, are extracted. Therefore, a tumbling detection model is established, and the model may be trained and self-adjusted continuously. In an experiment, a human body motion status and tumbling may be detected according to changes of tri-axis acceleration, and features that may be extracted include the following: low acceleration state and speed of tumbling, high-speed state of staggering before bumping, high-speed state of bumping, and maintenance time of each state; then a model for dynamically detecting human body tumbling is established according to the features to match tri-axis acceleration values of human body motion; and whether tumbling occurs is determined according to an output probability. Some parameters in the model may be adjusted according to stature, weight, and an amount of motion of a human body, and a real-time motion status of the human body.

For the calculated and obtained low acceleration threshold $a_0$, resultant acceleration sequence $I_0$ within the fixed time, curve area threshold $\Delta S$, and low acceleration time threshold $\Delta T$, the calculated and extracted low acceleration threshold $a_0$, resultant acceleration sequence $I_0$ within the fixed time, high acceleration threshold $a_1$, curve area threshold $\Delta S$, and low acceleration time threshold $\Delta T$ may be associated with human body status information corresponding to the sample, where the human body status information may include stature, weight, and/or motion status. The stature and weight may be an interval value.

Figure 3:
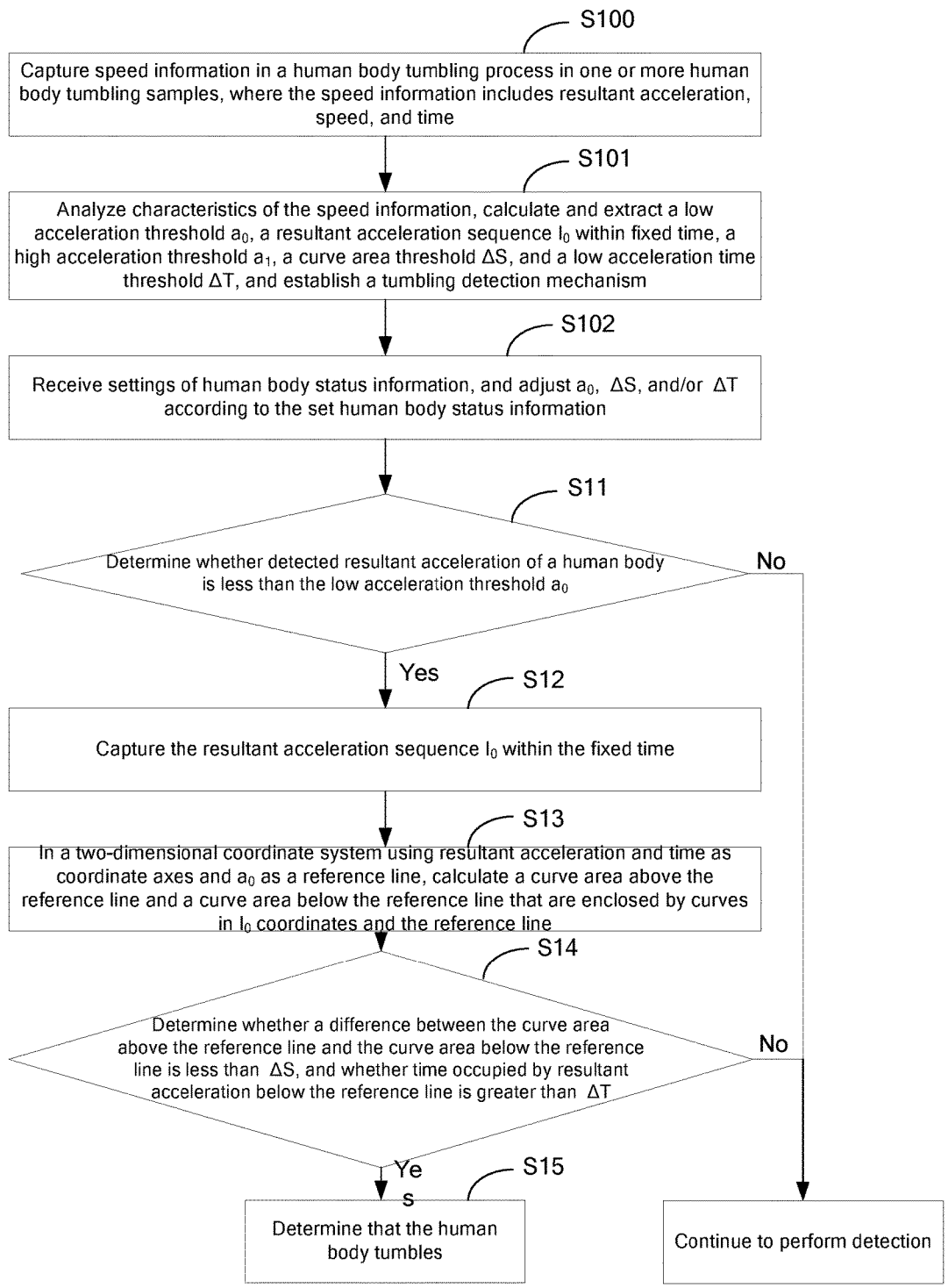
FIG. 3 is a schematic flowchart of steps of another embodiment of a human body tumbling detection method according to the present invention.

Referring to FIG. 3, in another embodiment of the present invention, before step S11 and after step S101, the method may further include:

Step S102: Receive settings of human body status information, and adjust $a_0$, $\Delta S$, and/or $\Delta T$ according to the set human body status information.

Because the parameters of the model may vary according to the stature and weight of a human body and the real-time motion status of the human body, each user may set human body status information of the user, and the detection device matches corresponding parameters $a_0$, $\Delta S$, and/or $\Delta T$, and the like according to the set human body status information.

In a specific use process, the method may further include: incorporating a human body tumbling sample detected by the device into the tumbling detection mechanism, and associating speed information of the sample with human body status information.

After accurately determining that a human body tumbling event occurs, the human body tumbling detection model may add the tumbling event to the human body tumbling detection model according to an acknowledgement of a user. For example, the speed information in the tumbling process is captured and analyzed, the low acceleration threshold $a_0$, the resultant acceleration sequence $I_0$ within the fixed time, the high acceleration threshold $a_1$, the curve area threshold $\Delta S$, and the low acceleration time threshold $\Delta T$ are extracted, and associated with the human body status information corresponding to the sample, and the tumbling detection mechanism is revised, so that a self-learning mechanism of the human body tumbling detection model is implemented.

Figure 4:
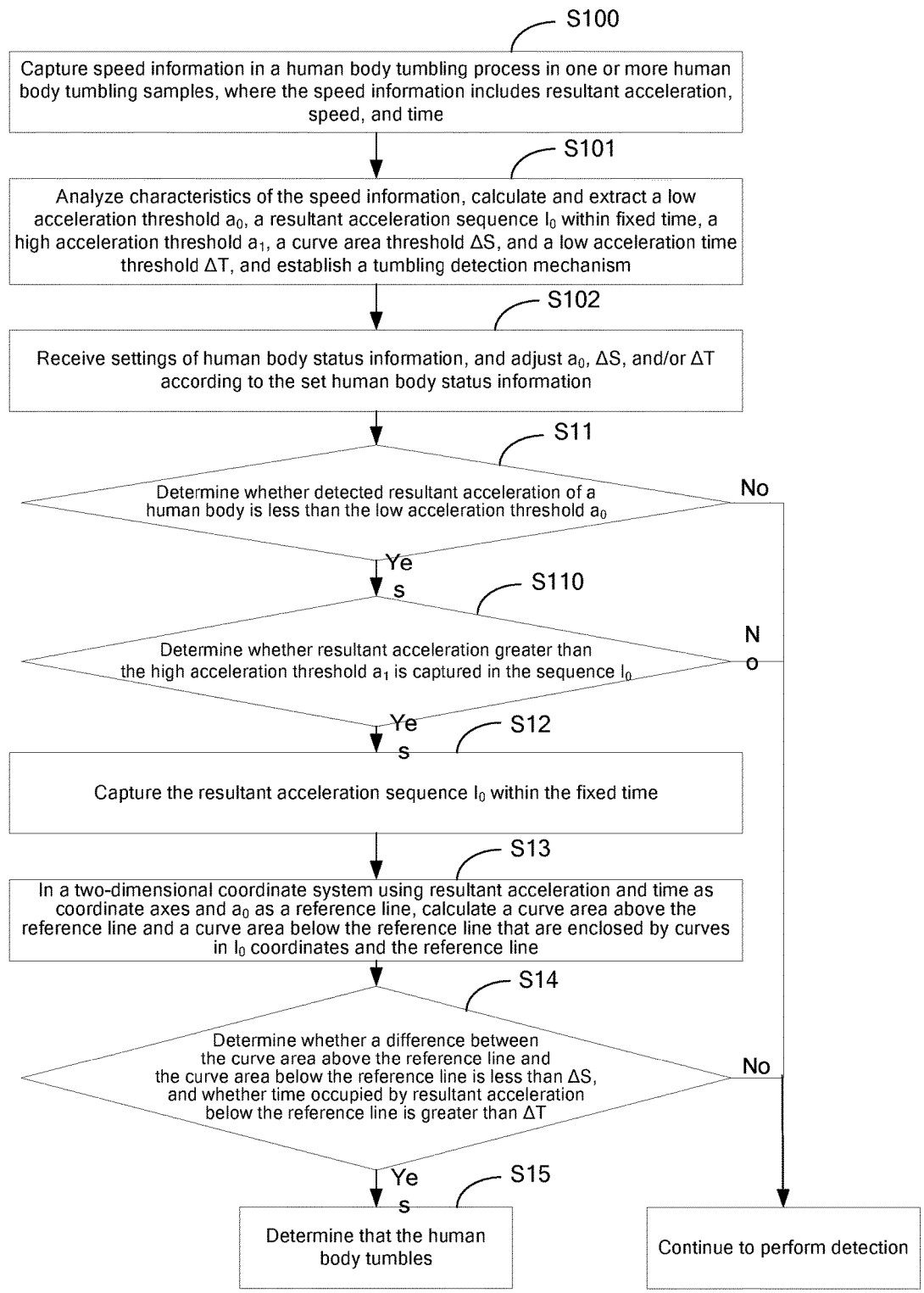
FIG. 4 is a schematic flowchart of steps of still another embodiment of a human body tumbling detection method according to the present invention.

Referring to FIG. 4, in still another embodiment of the present invention, after step S11, the method may further include:

Step S110: When capturing the resultant acceleration sequence $I_0$, determine whether resultant acceleration greater than the high acceleration threshold $a_1$ is captured in the sequence $I_0$; if yes, perform step S12; otherwise, continue to perform detection.

Before the human body tumbles, there is always a relatively long-time low acceleration process, and in addition, a case of high acceleration due to other external causes such as staggering may occur before tumbling or bumping. Therefore, high acceleration detection may be performed after a low acceleration process is detected. If a case in which resultant acceleration is greater than the high acceleration threshold $a_1$ occurs, the next step may continue to be performed to determine tumbling, or otherwise, it may be determined that tumbling does not occur, and initial resultant acceleration detection and determining are performed.

Figure 5:
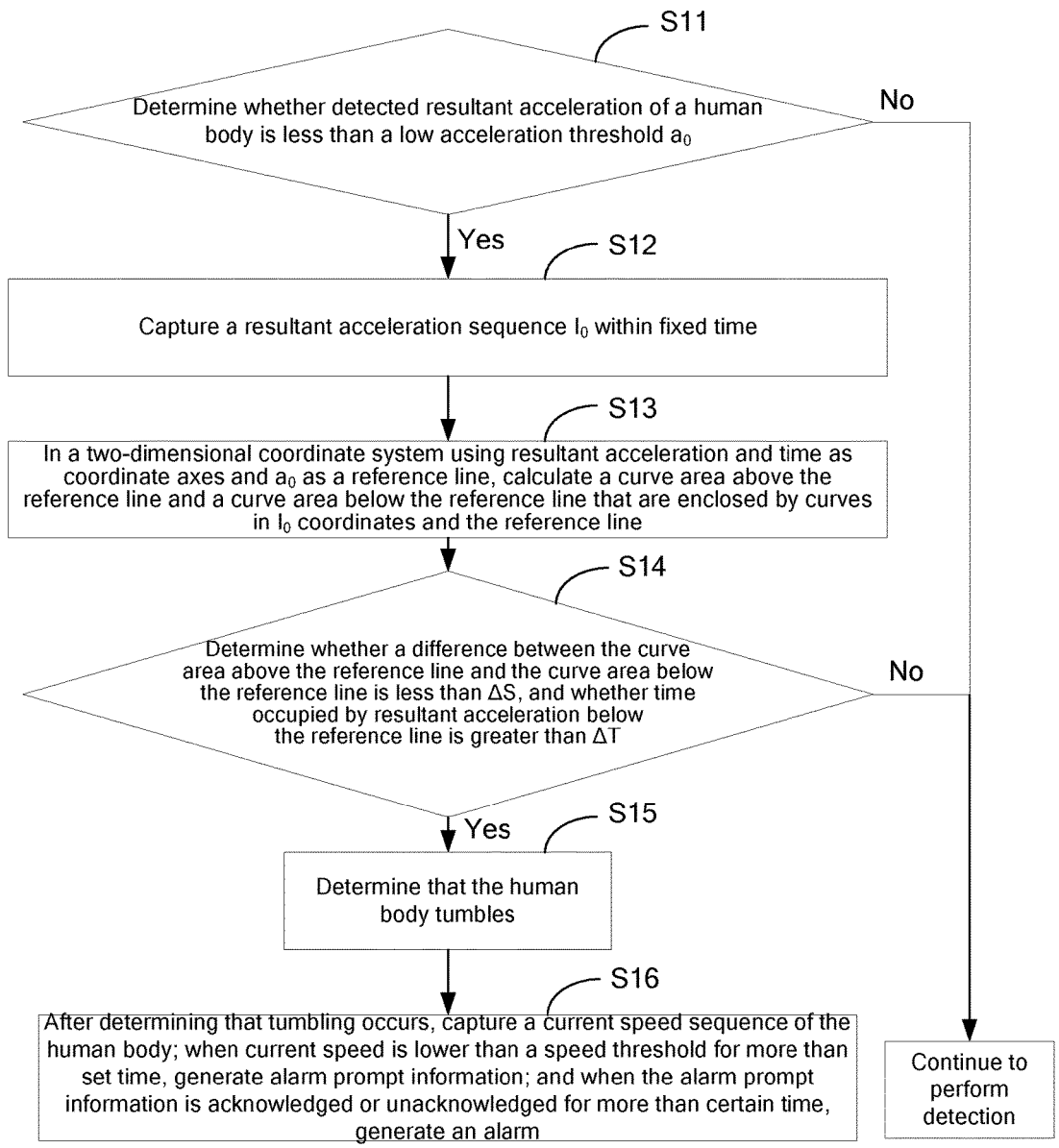
FIG. 5 is a schematic flowchart of steps of yet another embodiment of a human body tumbling detection method according to the present invention.

Referring to FIG. 5, in yet another embodiment of the present invention, after step S15, the method may further include:

Step S16: After determining that tumbling occurs, capture a current speed sequence of the human body; when current speed is lower than a speed threshold for more than set time, generate alarm prompt information; and when the alarm prompt information is acknowledged or unacknowledged for more than certain time, generate an alarm.

In this embodiment, during human body tumbling detection, first, initial speed of the human body may be 0 by default, and the speed of the human body at every moment may be calculated according to changes of tri-axis acceleration in which gravity acceleration is already considered. As the human body moves, the tri-axis acceleration changes continuously, and the speed also changes continuously. According to experimental data, an acceleration time sequence in a fixed time span may be acquired, where the time sequence may completely record acceleration values of a tumbling process (including a period of time before and after tumbling). Because there is a low acceleration state before the human body tumbles, a low acceleration threshold may also be obtained from experimental data. When acceleration of the human body in a moving process is lower than the low acceleration threshold, acceleration data may start to be captured and provided to the tumbling detection model for detection. Further, whether to continue to capture data or clear data is determined, and the time is recorded (that is, the foregoing time sequence begins). Because a high acceleration state caused by staggering or the like may occur before bumping during tumbling of the human body, after low acceleration is determined, high acceleration may be further determined. A high acceleration threshold is obtained according to experimental data. When acceleration of the human body in the moving process is higher than the high acceleration threshold, the detection model may start to be used to match the captured acceleration data. Then an operation may be performed according to the human body status information such as the set stature, weight, and/or motion status of the human body and the captured speed and acceleration information before or during the tumbling, and matching is performed with the parameters in the model. If the matching succeeds, it indicates that tumbling occurs, In this case, whether to generate an alarm is determined according to the speed information of the human body. If the speed of the human body is lower than the speed threshold for more than set time, alarm prompt information is generated. The user chooses, according to an actual situation, whether to generate an alarm. If the user does not perform any operation within certain time, an alarm is generated, and a short message notification and/or a call notification is initiated according to a preset contact phone number.

In addition, another high acceleration threshold may be obtained according to experimental data. When resultant acceleration of the human body is greater than the threshold, it is probable that the user receives instantaneous strong impact, for example, an event such as a vehicle accident occurs. If the resultant acceleration of the human body monitored in real time is greater than the threshold, alarm prompt information is generated directly, so that an alarm generation operation is performed in a case in which the user acknowledges the alarm prompt or the prompt times out.

Figure 6:
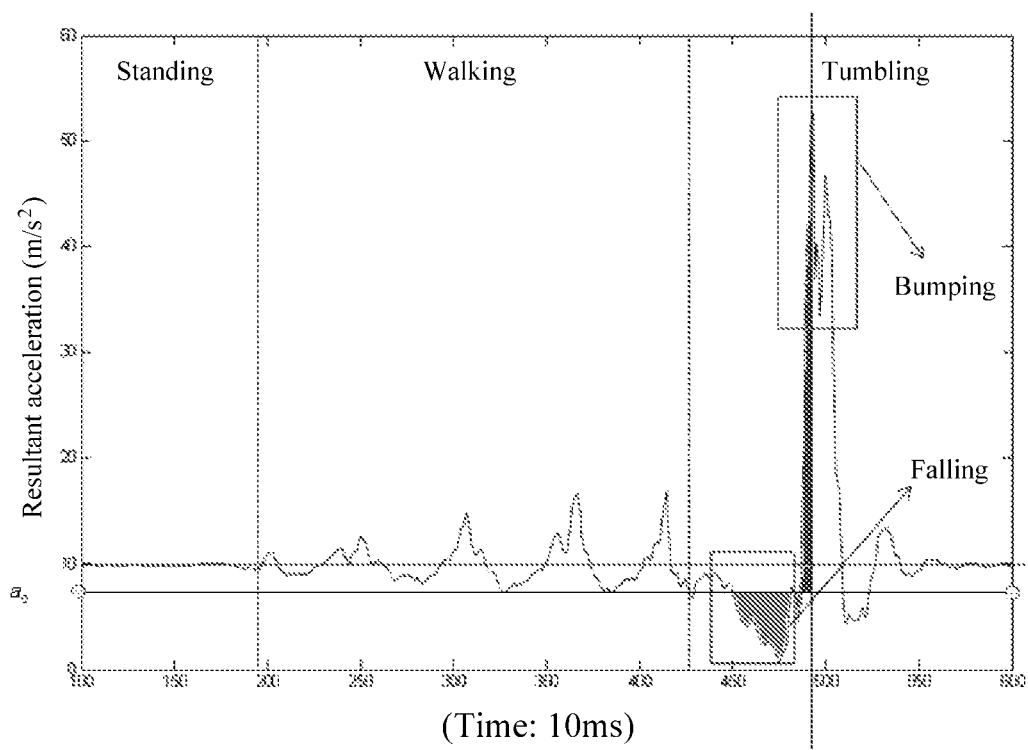
FIG. 6 is a schematic diagram of a two-dimensional coordinate system using time as a horizontal axis and resultant acceleration as a vertical axis in an embodiment of a human body tumbling detection method according to the present invention.

Referring to FIG. 6, FIG. 6 is a schematic diagram of a two-dimensional coordinate system using time (10 ms) as a horizontal axis and resultant acceleration (m/s$^2$) as a vertical axis, where the resultant acceleration threshold a0 is used as a reference line. It is shown that the resultant acceleration of the human body detected in the tumbling process changes with time. Within the time of 100 to approximately 190, the resultant acceleration is always approximately 10, which indicates that the user may be in a standing state. Within the time of approximately 190 to approximately 430, the resultant acceleration changes regularly and evenly above or below 10, and at this time, the resultant acceleration is always above a0, which indicates that the user may be in a normal walking state. Within the time of approximately 450 to approximately 490, first, a case of resultant acceleration lower than a0 occurs, and this continues from 450 to 480. Then a case of ephemeral high acceleration that is multiple times higher than a normal value (10) occurs, and this continues from 480 to 490. The case of low acceleration indicates that the user may be in a falling process before tumbling. The case of high acceleration indicates that the user may be in a bumping process after tumbling. From the figure, it may be obviously seen that in the tumbling process, a curve area that is below the reference line and enclosed by a curve formed by the resultant acceleration in the coordinates and the reference line, is greater than a curve area above the reference line.

A manner of calculation and matching in the tumbling detection model is as follows: First, the low acceleration threshold $a_0$ is determined through an experiment and research; when a resultant acceleration value generated in the moving process of the human body is lower than $a_0$, the device is triggered to start to capture data of the tri-axis accelerometer in a fixed acceleration time sequence $l_0$; in addition, the following calculation is performed: an acceleration curve area based on the reference line $a_0$, from a moment of capturing data, is calculated; the area that is above the reference line and enclosed by the acceleration and the reference line ais positive, or otherwise, is negative; the total curve area is equal to the curve area above the reference line plus the curve area below the reference line (that is, equal to a difference between the curve area above the reference line and the curve area below the reference line in a case in which both are positive); and so long as the obtained curve area is less than $\Delta S$, and a sum of time of acceleration lower than the acceleration threshold $a_0$ in $I_0$ is greater than $\Delta T$, this may be considered as a process of tumbling before bumping. $\Delta T$, $\Delta S$, and $a_0$ may be dynamically adjusted according to the weight, stature, and motion status (amount of motion) of the user.

Human body tumbling detection performed according to acceleration is described above. In this embodiment, detection may also be performed according to acceleration and speed. When detected acceleration is lower than the low acceleration threshold, first, there is an acceleration and speed sequence in a fixed time span. The time span of the sequence may be sufficient to include a normal moving process of the user before tumbling in a complete tumbling process. By default, initial speed of the user is zero. Approximate speed of the human body at a moment may be calculated according to tri-axis acceleration and time. In addition, the current motion intensity and current status of the user may be obtained according to the acceleration and speed sequence in the fixed time span, and accordingly, some related parameters for tumbling verification may be adjusted, so that the model can more accurately detect the status before tumbling.

The human body tumbling detection method may be based on a device that has acceleration detection and communication functions such as a smartphone. So long as a user carries a smartphone installed with an application for human body tumbling detection, the application automatically captures and analyzes human body dynamics information based on different features of kinematics and dynamics in safe moving and tumbling of a human body, determines whether the human body tumbles, and generates an alarm notification such as a short message or a call by using advantages of mobile phone communication. In comparison with other tumbling detection devices that need to be purchased or provided additionally, the device according to the present invention has relatively high applicability, featuring a wide range of use, a low price, and portability. Most importantly, motion behavior characteristics of the human body are fully considered, and therefore, a detection rate is increased, and a wrong determining rate is reduced.

Figure 7:
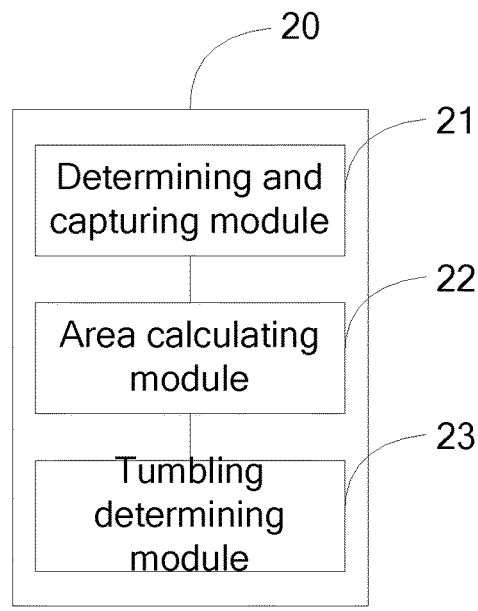
FIG. 7 is a schematic structural diagram of an embodiment of a human body tumbling detection device according to the present invention.

Referring to FIG. 7, an embodiment of a human body tumbling detection device 20 according to the present invention is provided. The device 20 may include a determining and capturing module 21, an area calculating module 22, and a tumbling determining module 23. The determining and capturing module 21 is configured to capture a resultant acceleration sequence $I_0$ within fixed time when detecting that resultant acceleration of a human body is less than a low acceleration threshold $a_0$. The area calculating module 22 is configured to calculate, in a two-dimensional coordinate system using resultant acceleration and time as coordinate axes and $a_0$ as a reference line, a curve area above the reference line and a curve area below the reference line that are enclosed by curves in $I_0$ coordinates and the reference line. The tumbling determining module 23 is configured to determine, when a difference between the curve area above the reference line and the curve area below the reference line is less than a curve area threshold $\Delta S$, and time occupied by resultant acceleration below the reference line is greater than a low acceleration time threshold $\Delta T$, that the human body tumbles.

In view of the problems that exist in the conventional tumbling detection technologies and detection devices 20, the human body tumbling detection device 20 provided by the present invention can automatically detect acceleration information and speed information of a human body by using a sensor, correctly determine, according to the acceleration, speed, motion time, and motion status of the human body, whether the human body has tumbled, and prompts whether to generate an alarm for help, and can perform operations such as acknowledging the prompt or canceling the alarm for help.

A device for implementing the human body tumbling detection device 20 needs to be equipped with at least an accelerometer (for example, a tri-axis accelerometer), and when an emergency help function needs to be implemented, may be further equipped with a communication module (for example, a GSM module or a CDMA module for mobile communication). For portability and ease of use, the device may be a mobile terminal, for example, a common mobile terminal device such as a smartphone or a tablet computer. The human body tumbling detection device 20 may be disposed in a mobile terminal. Such common mobile terminal devices are generally equipped with a communication module and an accelerometer, and therefore may be used directly, and no additional configuration is required.

Figure 8:
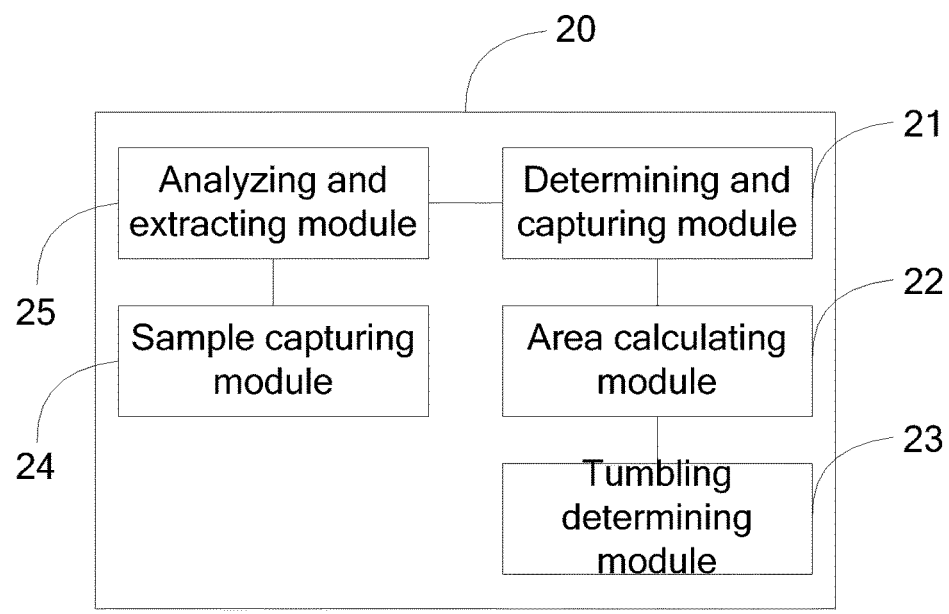
FIG. 8 is another schematic structural diagram of an embodiment of a human body tumbling detection device according to the present invention.

Referring to FIG. 8, the device 20 may further include a sample capturing module 24 and an analyzing and extracting module 25. The sample capturing module 24 is configured to capture speed information in a human body tumbling process in one or more human body tumbling samples, where the speed information includes resultant acceleration, speed, and time. The analyzing and extracting module 25 is configured to analyze characteristics of the speed information, calculate and extract the low acceleration threshold $a_0$, the resultant acceleration sequence $I_0$ within the fixed time, a high acceleration threshold $a_1$, the curve area threshold $\Delta S$, and the low acceleration time threshold $\Delta T$, and establish a tumbling detection mechanism.

Before tumbling detection is implemented, first, several tumbling experiments are performed to capture speed information in a human body tumbling process, where the speed information includes resultant acceleration, speed, and time. Further, an acceleration time sequence before tumbling and bumping may be recorded, some acceleration features are extracted, and a tumbling detection model is established. The model may be trained and optimized continuously by using tumbling data.

Establishment of a tumbling detection model is a most important part for implementing accurate tumbling detection. First, acceleration data related to a tumbling process is acquired according to some experiments and related tumbling data. The acceleration data is analyzed, filtered, and integrated, and features of kinematics and dynamics in human body tumbling, for example, long-time low acceleration before tumbling and possible staggering before tumbling, are extracted. Therefore, a tumbling detection model is established, and the model may be trained and self-adjusted continuously. In an experiment, a human body motion status and tumbling may be detected according to changes of tri-axis acceleration, and features that may be extracted include the following: low acceleration state and speed of tumbling, high-speed state of staggering before bumping, high-speed state of bumping, and maintenance time of each state; then a model for dynamically detecting human body tumbling is established according to the features to match tri-axis acceleration values of human body motion; and whether tumbling occurs is determined according to an output probability. Some parameters in the model may be adjusted according to stature, weight, and an amount of motion of a human body, and a real-time motion status of the human body.

The analyzing and extracting module 25 may be further configured to associate the calculated and extracted low acceleration threshold $a_0$, resultant acceleration sequence $I_0$ in the fixed time, high acceleration threshold $a_1$, curve area threshold $\Delta S$, and low acceleration time threshold $\Delta T$ with human body status information corresponding to the sample, where the human body status information includes stature, weight, and/or motion status. The stature and weight may be an interval value.

Figure 9:
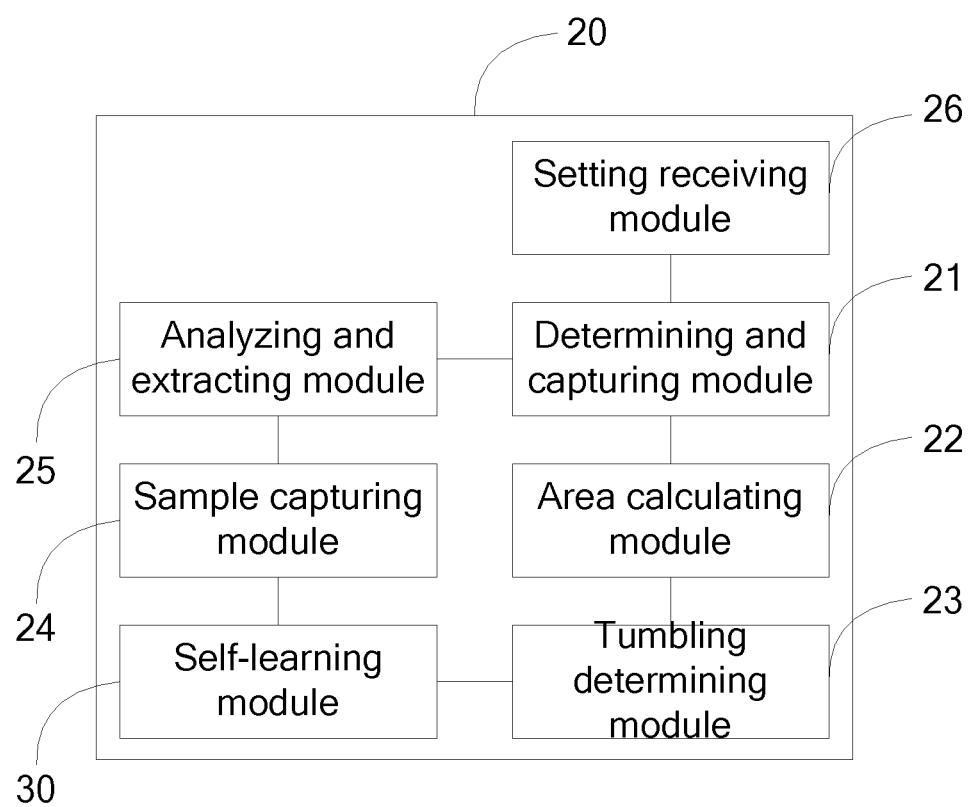
FIG. 9 is a schematic structural diagram of another embodiment of a human body tumbling detection device according to the present invention.

Referring to FIG. 9, in another embodiment of the present invention, the device 20 may further include a setting receiving module 26, configured to receive settings of human body status information, and adjust $a_0$, $\Delta S$, and/or $\Delta T$ according to the set human body status information.

Because the parameters of the model may vary according to the stature and weight of a human body and the real-time motion status of the human body, each user may set human body status information of the user, and the detection device matches corresponding parameters $a_0$, $\Delta S$, and/or $\Delta T$, and the like according to the set human body status information.

The device 20 may further include a self-learning module 30, configured to incorporate a human body tumbling sample detected by the device into the tumbling detection mechanism, and associate speed information of the sample with human body status information.

After accurately determining that a human body tumbling event occurs, the human body tumbling detection model may add the tumbling event to the human body tumbling detection model according to an acknowledgement of a user. For example, the speed information in the tumbling process is captured and analyzed, the low acceleration threshold $a_0$, the resultant acceleration sequence $I_0$ within the fixed time, the high acceleration threshold $a_1$, the curve area threshold $\Delta S$, and the low acceleration time threshold $\Delta T$ are extracted, and associated with the human body status information corresponding to the sample, and the tumbling detection mechanism is revised, so that a self-learning mechanism of the human body tumbling detection model is implemented.

Figure 10:
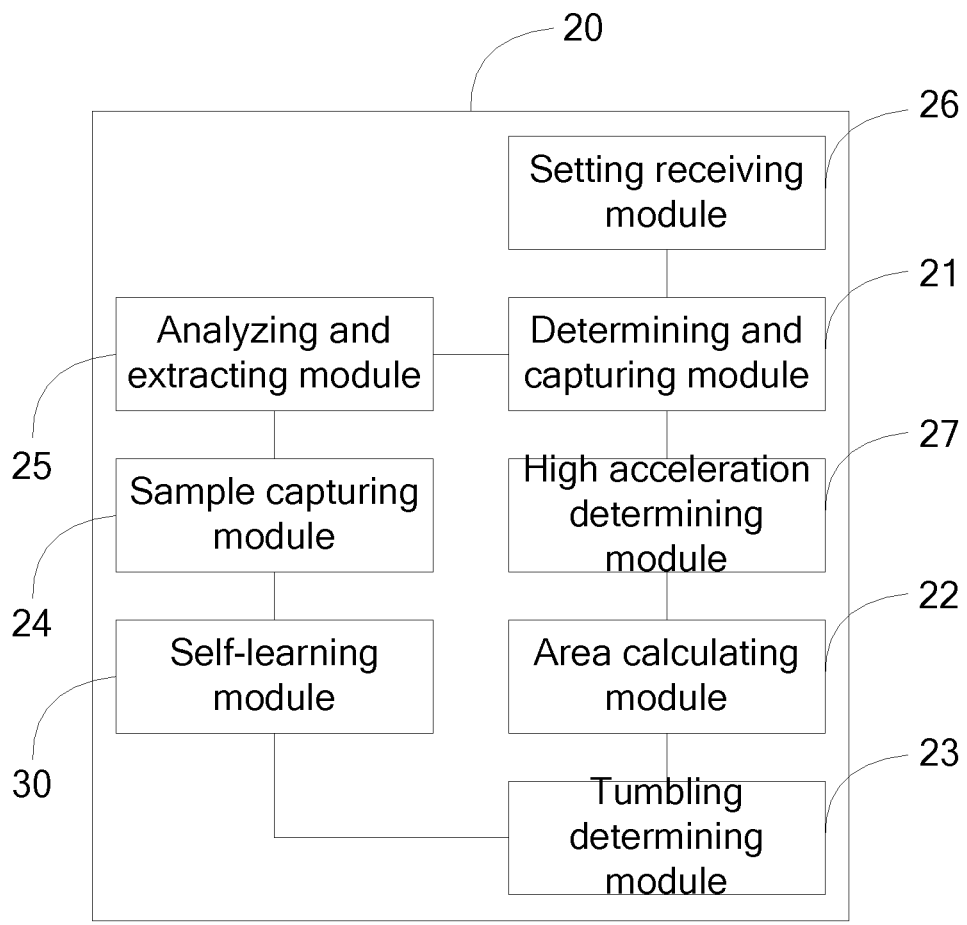
FIG. 10 is a schematic structural diagram of still another embodiment of a human body tumbling detection device according to the present invention.

Referring to FIG. 10, in still another embodiment of the present invention, the device 20 may further include a high acceleration determining module 27, configured to: when the resultant acceleration sequence $I_0$ is captured, determine whether resultant acceleration greater than a high acceleration threshold $a_1$ is captured in the sequence $I_0$, and if yes, calculate the curve areas by using the area calculating module 22.

Before the human body tumbles, there is always a relatively long-time low acceleration process, and in addition, a case of high acceleration due to other external causes such as staggering may occur before tumbling or bumping. Therefore, high acceleration detection may be performed after a low acceleration process is detected. If a case in which resultant acceleration is greater than the high acceleration threshold $a_1$ occurs, the next step may continue to be performed to determine tumbling, or otherwise, it may be determined that tumbling does not occur, and initial resultant acceleration detection and determining are performed.

Figure 11:
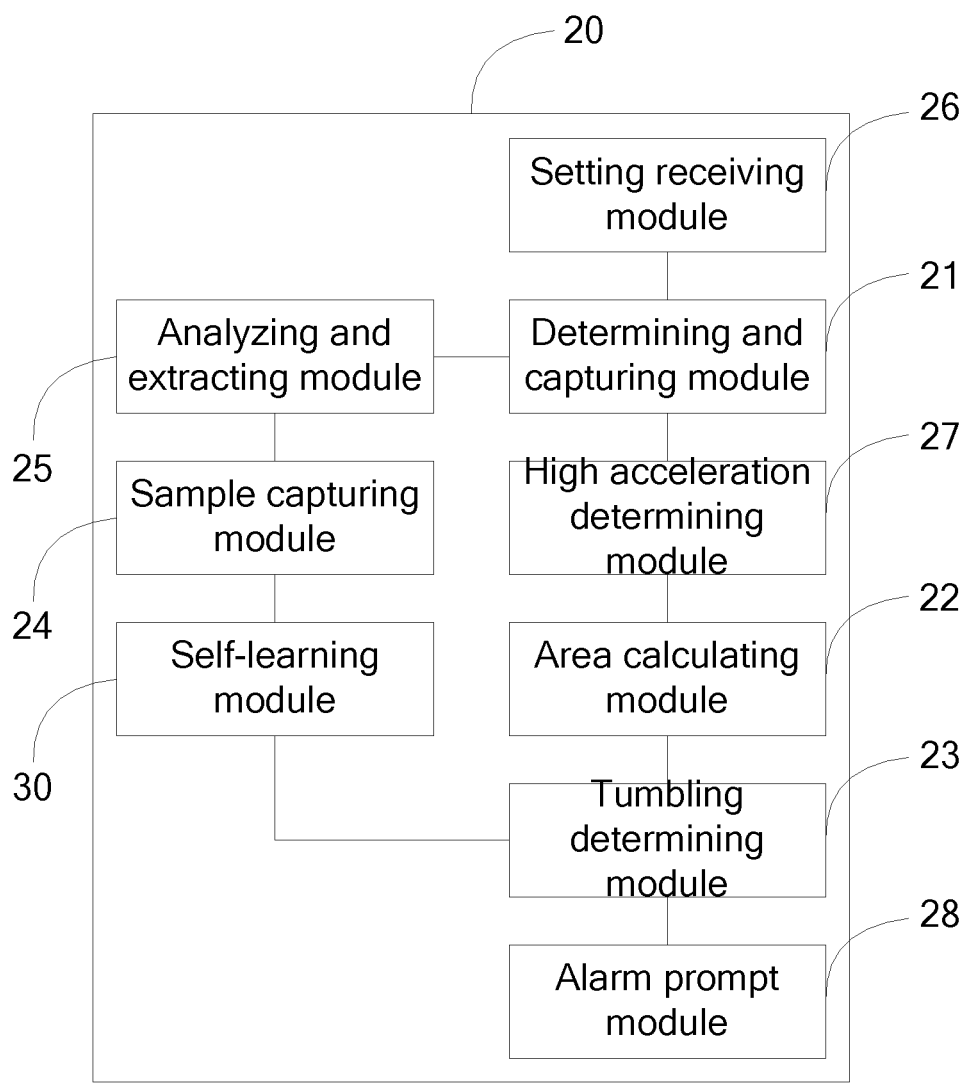
FIG. 11 is a schematic structural diagram of yet another embodiment of a human body tumbling detection device according to the present invention.

Referring to FIG. 11, in yet another embodiment of the present invention, the device may further include an alarm prompt module 28, configured to: after it is determined that tumbling occurs, capture a current speed sequence of the human body; when current speed is lower than a speed threshold for more than set time, generate alarm prompt information; and when the alarm prompt information is acknowledged or unacknowledged for more than certain time, generate an alarm.

In this embodiment, during human body tumbling detection, first, initial speed of the human body may be 0 by default, and the speed of the human body at every moment may be calculated according to changes of tri-axis acceleration in which gravity acceleration is already considered. As the human body moves, the tri-axis acceleration changes continuously, and the speed also changes continuously. According to experimental data, an acceleration time sequence in a fixed time span may be acquired, where the time sequence may completely record acceleration values of a tumbling process (including a period of time before and after tumbling). Because there is a low acceleration state before the human body tumbles, a low acceleration threshold may also be obtained from experimental data. When acceleration of the human body in a moving process is lower than the low acceleration threshold, acceleration data may start to be captured and provided to the tumbling detection model for detection. Further, whether to continue to capture data or clear data is determined, and the time is recorded (that is, the foregoing time sequence begins). Because a high acceleration state caused by staggering or the like may occur before bumping during tumbling of the human body, after low acceleration is determined, high acceleration may be further determined. A high acceleration threshold is obtained according to experimental data. When acceleration of the human body in the moving process is higher than the high acceleration threshold, the detection model may start to be used to match the captured acceleration data. Then an operation may be performed according to the human body status information such as the set stature, weight, and/or motion status of the human body and the captured speed and acceleration information before or during the tumbling, and matching is performed with the parameters in the model. If the matching succeeds, it indicates that tumbling occurs, in this case, whether to generate an alarm is determined according to the speed information of the human body. If the speed of the human body is lower than the speed threshold for more than set time, alarm prompt information is generated. The user chooses, according to an actual situation, whether to generate an alarm. If the user does not perform any operation within certain time, an alarm is generated, and a short message notification and/or a call notification is initiated according to a preset contact phone number.

In addition, another high acceleration threshold may be obtained according to experimental data. When resultant acceleration of the human body is greater than the threshold, it is probable that the user receives instantaneous strong impact, for example, an event such as a vehicle accident occurs. If the resultant acceleration of the human body monitored in real time is greater than the threshold, alarm prompt information is generated directly, so that an alarm generation operation is performed by a communication component in a case in which the user acknowledges the alarm prompt or the prompt times out.

Referring to FIG. 6, FIG. 6 is a schematic diagram of a two-dimensional coordinate system using time (10 ms) as a horizontal axis and resultant acceleration (m/s$^2$) as a vertical axis, where the resultant acceleration threshold a0 is used as a reference line. It is shown that the resultant acceleration of the human body detected in the tumbling process changes with time. Within the time of 100 to approximately 190, the resultant acceleration is always approximately 10, which indicates that the user may be in a standing state. Within the time of approximately 190 to approximately 430, the resultant acceleration changes regularly and evenly above or below 10, and at this time, the resultant acceleration is always above a0, which indicates that the user may be in a normal walking state. Within the time of approximately 450 to approximately 490, first, a case of resultant acceleration lower than a0 occurs, and this continues from 450 to 480. Then a case of ephemeral high acceleration that is multiple times higher than a normal value (10) occurs, and this continues from 480 to 490. The case of low acceleration indicates that the user may be in a falling process before tumbling. The case of high acceleration indicates that the user may be in a bumping process after tumbling. From the figure, it may be obviously seen that in the tumbling process, a curve area that is below the reference line and enclosed by a curve formed by the resultant acceleration in the coordinates and the reference line, is greater than a curve area above the reference line.

A manner of calculation and matching in the tumbling detection model is as follows: First, the low acceleration threshold $a_0$ is determined through an experiment and research; when a resultant acceleration value generated in the moving process of the human body is lower than $a_0$, the device is triggered to start to capture data of the tri-axis accelerometer in a fixed acceleration time sequence $a_0$; in addition, the following calculation is performed: an acceleration curve area based on the reference line $l_0$, from a moment of capturing data, is calculated; the area that is above the reference line and enclosed by the acceleration and the reference line $a_0$ is positive, or otherwise, is negative; the total curve area is equal to the curve area above the reference line plus the curve area below the reference line (that is, equal to a difference between the curve area above the reference line and the curve area below the reference line in a case in which both are positive); and so long as the obtained curve area is less than $a_0$, and a sum of time of acceleration lower than the acceleration threshold $\Delta S$ in $l_0$ is greater than $a_0$, this may be considered as a process of tumbling before bumping. $\Delta T$, $\Delta S$, and $a_0$ may be dynamically adjusted according to the weight, stature, and motion status (amount of motion) of the user.

Human body tumbling detection performed according to acceleration is described above. In this embodiment, detection may also be performed according to acceleration and speed. When detected acceleration is lower than the low acceleration threshold, first, there is an acceleration and speed sequence in a fixed time span. The time span of the sequence may be sufficient to include a normal moving process of the user before tumbling in a complete tumbling process. By default, initial speed of the user is zero. Approximate speed of the human body at a moment may be calculated according to tri-axis acceleration and time. In addition, the current motion intensity and current status of the user may be obtained according to the acceleration and speed sequence in the fixed time span, and accordingly, some related parameters for tumbling verification may be adjusted, so that the model can more accurately detect the status before tumbling.

The human body tumbling detection device 20 may be based on a device that has acceleration detection and communication functions such as a smartphone. So long as a user carries a smartphone installed with an application for human body tumbling detection, the application automatically captures and analyzes human body dynamics information based on different features of kinematics and dynamics in safe moving and tumbling of a human body, determines whether the human body tumbles, and generates an alarm notification such as a short message or a call by using advantages of mobile phone communication. In comparison with other tumbling detection devices that need to be purchased or provided additionally, the device according to the present invention has relatively high applicability, featuring a wide range of use, a low price, and portability. Most importantly, motion behavior characteristics of the human body are fully considered, and therefore, a detection rate is increased, and a wrong determining rate is reduced.

Figure 12:
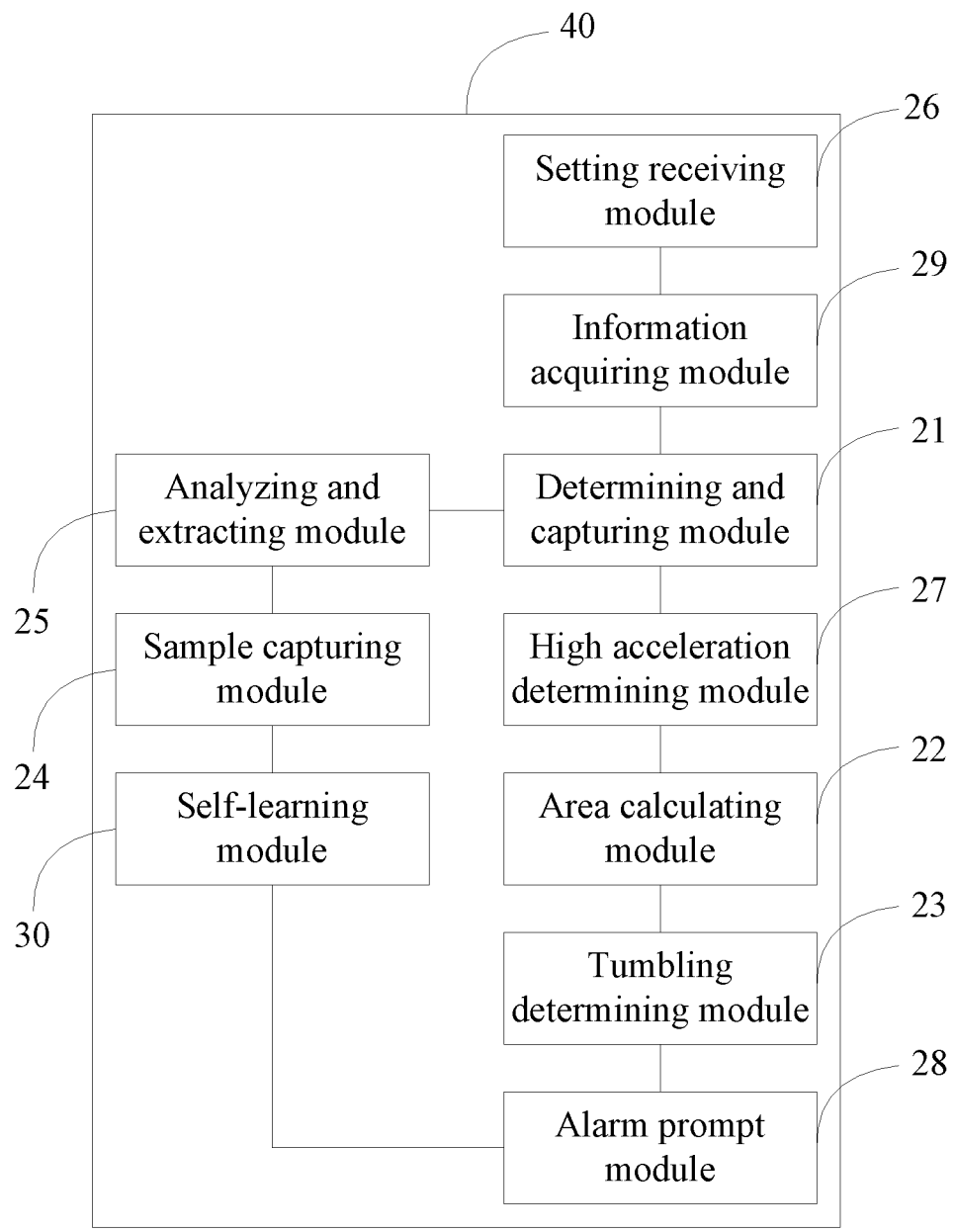
FIG. 12 is a schematic structural diagram of an embodiment of a mobile terminal system according to the present invention.

Referring to FIG. 12, an embodiment of a mobile terminal system 40 according to the present invention is provided. The mobile terminal system 40 may include an information acquiring module 29, a determining and capturing module 21, an area calculating module 22, a tumbling determining module 23, and an alarm prompt module 28. The information acquiring module 29 is configured to acquire speed information by using a tri-axis accelerometer. The determining and capturing module 21 is configured to capture a resultant acceleration sequence $I_0$ within fixed time when detecting that resultant acceleration of a human body is less than a low acceleration threshold $a_0$. The area calculating module 22 is configured to calculate, in a two-dimensional coordinate system using resultant acceleration and time as coordinate axes and $a_0$ as a reference line, a curve area above the reference line and a curve area below the reference line that are enclosed by curves in $I_0$ coordinates and the reference line. The tumbling determining module 23 is configured to determine, when a difference between the curve area above the reference line and the curve area below the reference line is less than a curve area threshold $\Delta S$, and time occupied by resultant acceleration below the reference line is greater than a low acceleration time threshold $\Delta T$, that the human body tumbles. The alarm prompt module 28 is configured to: after it is determined that tumbling occurs, capture a current speed sequence of the human body; when current speed is lower than a speed threshold for more than set time, generate alarm prompt information; and when the alarm prompt information is acknowledged or unacknowledged for more than certain time, generate an alarm by using a mobile communication component.

The mobile terminal system 40 may further include a sample capturing module 24, an analyzing and extracting module 25, a high acceleration determining module 27, a setting receiving module 26, and a self-learning module 30. The determining and capturing module 21, area calculating module 22, tumbling determining module 23, sample capturing module 24, analyzing and extracting module 25, high acceleration determining module 27, setting receiving module 26, alarm prompt module 28, and self-learning module 30 may be the same as those described in the foregoing embodiment.

The mobile terminal system 40 may be based on a device that has acceleration detection and communication functions such as a smartphone. So long as a user carries a smartphone installed with an application for human body tumbling detection, the application automatically captures and analyzes human body dynamics information based on different features of kinematics and dynamics in safe moving and tumbling of a human body, determines whether the human body tumbles, and generates an alarm notification such as a short message or a call by using advantages of mobile phone communication. In comparison with other tumbling detection devices that need to be purchased or provided additionally, the device according to the present invention has relatively high applicability, featuring a wide range of use, a low price, and portability. Most importantly, motion behavior characteristics of the human body are fully considered, and therefore, a detection rate is increased, and a wrong determining rate is reduced.

The foregoing descriptions are only exemplary embodiments of the present invention, and are not intended to limit the patent scope of the present invention. Any equivalent structure or equivalent process transformation made by using the specification of the present invention and content of the accompanying drawings, or used directly or indirectly in other related technical fields, shall also be covered in the patent protection scope of the present invention.

What is claimed is:

1. A human body tumbling detection method using a portable smart mobile device, the method comprising at least one microprocessor, an acceleration sensor, a speed sensor and a memory of the portable smart mobile device executing the steps of: when detecting that resultant acceleration of a human body is less than a low acceleration threshold $a_0$ set and stored in the memory according to human body status information, capturing a resultant acceleration sequence $I_0$ within a fixed time;

in a two-dimensional coordinate system using resultant acceleration and time as coordinate axes and $a_0$ as a reference line, calculating a curve area above the reference line and a curve area below the reference line that are enclosed by curves in $I_0$ coordinates and the reference line;

when a difference between the curve area above the reference line and the curve area below the reference line is less than a curve area threshold $\Delta S$, and time occupied by resultant acceleration below the reference line is greater than a low acceleration time threshold $\Delta T$, determining that the human body tumbles;

after determining that tumbling occurs, capturing a current speed sequence of the human body; when the current speed is lower than a speed threshold for more than a set time, generating an alarm prompt information; and when the alarm prompt information is acknowledged or unacknowledged for more than a certain period of time, generating an alarm; and wherein the low acceleration threshold $a_0$, the curve area threshold $\Delta S$, the low acceleration time threshold $\Delta T$ and the speed threshold are respectively set and stored in the memory according to human body status information.

2. The human body tumbling detection method according to claim 1, wherein before the step of capturing a resultant acceleration sequence $I_0$ within the fixed time when detecting that resultant acceleration of a human body is less than a low acceleration threshold $a_0$, the method further comprises: capturing speed information transmitted from the speed sensor in a human body tumbling process in one or more human body tumbling samples, wherein the speed information comprises resultant acceleration, speed, and time; and analyzing characteristics of the speed information, calculating and extracting the low acceleration threshold $a_0$, the resultant acceleration sequence $I_0$ within the fixed time, a high acceleration threshold $a_1$, the curve area threshold $\Delta S$, and the low acceleration time threshold $\Delta T$, and establishing a tumbling detection mechanism.

3. The human body tumbling detection method according to claim 2, wherein the step of analyzing characteristics of the speed information, calculating and extracting the low acceleration threshold $a_0$, the resultant acceleration sequence $I_0$ within the fixed time, a high acceleration threshold $a_1$, the curve area threshold $\Delta S$, and the low acceleration time threshold $\Delta T$ further comprises: associating the calculated and extracted low acceleration threshold $a_0$, the resultant acceleration sequence $I_0$ within the fixed time, the high acceleration threshold $a_1$, the curve area threshold $\Delta S$, and the low acceleration time threshold $\Delta T$ with human body status information corresponding to the samples stored in the memory, wherein the human body status information comprises stature, weight, and/or motion status.

4. The human body tumbling detection method according to claim 1, wherein after the step of capturing a resultant acceleration sequence $I_0$ within the fixed time when detecting that resultant acceleration of a human body is less than a low acceleration threshold $a_0$, the method further comprises: when capturing the resultant acceleration sequence $I_0$, determining whether resultant acceleration greater than the high acceleration threshold $a_1$ is captured in the resultant acceleration sequence $I_0$, and if yes to the resultant acceleration greater than the high acceleration threshold $a_1$ is captured in the resultant acceleration sequence $I_0$, performing the next step of capturing the resultant acceleration sequence $I_0$ within the fixed time.

5. The human body tumbling detection method according to claim 1, wherein before the step of capturing a resultant acceleration sequence $I_0$ within the fixed time when detecting that resultant acceleration of a human body is less than a low acceleration threshold $a_0$ stored in the memory, the method further comprises: receiving settings of the human body status information from the memory, and adjusting $a_0$, $\Delta S$, and/or $\Delta T$ according to the set human body status information.

6. A human body tumbling detection device comprising at least one microprocessor, an acceleration sensor, a speed sensor and a memory, with a low acceleration threshold $a_0$, a curve area threshold $\Delta S$, a low acceleration time threshold $\Delta T$ and a speed threshold respectively set and stored in the memory according to human body status information, the at least one microprocessor comprising:

a determining and capturing module, configured to capture a resultant acceleration sequence $I_0$ within a fixed time when detecting that resultant acceleration of a human body transmitted from the acceleration sensor is less than the low acceleration threshold $a_0$;

an area calculating module, configured to calculate, in a two-dimensional coordinate system using resultant acceleration and time as coordinate axes and $a_0$ as a reference line, a curve area above the reference line and a curve area below the reference line that are enclosed by curves in $I_0$ coordinates and the reference line;

a tumbling determining module, configured to determine, when a difference between the curve area above the reference line and the curve area below the reference line is less than the curve area threshold $\Delta S$, and time occupied by resultant acceleration below the reference line is greater than the low acceleration time threshold $\Delta T$, that the human body tumbles; and an alarm prompt module, configured to: after determining that tumbling occurs, capture a current speed sequence of the human body; when the current speed is lower than the speed threshold for more than a set time, generating an alarm prompt information: and when the alarm prompt information is acknowledged or unacknowledged for more than a certain period of time, generating an alarm.

7. The human body tumbling detection device according to claim 6, wherein the device further comprises: a sample capturing module, configured to capture speed information transmitted from the speed sensor in a human body tumbling process in one or more human body tumbling samples, wherein the speed information comprises resultant acceleration, speed, and time; and an analyzing and extracting module, configured to analyze characteristics of the speed information, calculate and extract the low acceleration threshold $a_0$, the resultant acceleration sequence $I_0$ within the fixed time, a high acceleration threshold $a_1$, the curve area threshold $\Delta S$, and the low acceleration time threshold $\Delta T$, and establish a tumbling detection mechanism.

8. The human body tumbling detection device according to claim 7, wherein the analyzing and extracting module is further configured to: associate the calculated and extracted the low acceleration threshold $a_0$, the resultant acceleration sequence $I_0$ within the fixed time, the high acceleration threshold $a_1$, the curve area threshold $\Delta S$, and the low acceleration time threshold $\Delta T$ with human body status information corresponding to the samples stored in the memory, wherein the human body status information comprises stature, weight, and/or motion status.

9. The human body tumbling detection device according to claim 6, wherein the device further comprises: a high acceleration determining module, configured to:
when the resultant acceleration sequence $I_0$ is captured, determine whether resultant acceleration greater than a high acceleration threshold $a_1$ is captured in the resultant acceleration sequence $I_0$, and if the resultant acceleration greater than the high acceleration threshold $a_1$ is captured in the resultant acceleration sequence $I_0$, then calculate the curve areas by using the area calculating module.

10. The human body tumbling detection device according to claim 6, wherein the device further comprises: a setting receiving module, configured to receive settings of the human body status information from the memory, and adjust $a_0$, $\Delta S$, and/or $\Delta T$ according, to the set human body status information.

11. A mobile terminal system comprising at least one microprocessor, a memory and a tri-axis accelerometer, with a low acceleration threshold $a_0$, a curve area threshold $\Delta S$, a low acceleration time threshold $\Delta T$ and a speed threshold respectively set and stored in the memory according to human body status information, the at least one microprocessor comprising:
an information acquiring module, configured to acquire speed information by using the tri-axis accelerometer;
a determining and capturing module, configured to capture a resultant acceleration sequence $I_0$ within a fixed time when detecting that resultant acceleration of a human body transmitted from the tri-axis accelerometer is less than the low acceleration threshold $a_0$;
an area calculating module, configured to calculate, in a two-dimensional coordinate system using resultant acceleration and time as coordinate axes and $a_0$ as a reference line, a curve area above the reference line and a curve area below the reference line that are enclosed by curves in $I_0$ coordinates and the reference line;
a tumbling determining module, configured to determine, when a difference between the curve area above the reference line and the curve area below the reference line is less than the curve area threshold $\Delta S$, and time occupied by resultant acceleration below the reference line is greater than the low acceleration time threshold $\Delta T$, that the human body tumbles; and
an alarm prompt module, configured to: after determining that tumbling occurs, capture a current speed sequence of the human body; when the current speed is lower than the speed threshold for more than a set time, generate an alarm prompt information; and when the alarm prompt information is acknowledged or unacknowledged for more than a certain period of time, generate an alarm by using a mobile communication component.

12. The mobile terminal system according to claim 11, wherein the mobile terminal system further comprises: a high acceleration determining module, configured to: when the resultant acceleration sequence $I_0$ is captured, determine whether resultant acceleration greater than a high acceleration threshold $a_1$ is captured in the resultant acceleration sequence $I_0$, and if the resultant acceleration greater than the high acceleration threshold $a_1$ is captured in the resultant acceleration sequence $I_0$, then calculate the curve areas by using the area calculating module.

* * * * *